United States Patent [19]
Randad et al.

[11] Patent Number: 5,763,464
[45] Date of Patent: Jun. 9, 1998

[54] RETROVIRAL AGENTS CONTAINING ANTHRANILAMIDE, SUBSTITUTED BENZAMIDE AND OTHER SUBUNITS, AND METHODS OF USING SAME

[75] Inventors: Ramnarayan S. Randad; John W. Erickson, both of Frederick; Talapadi N. Bhat, South Potomac, all of Md.

[73] Assignee: The United States of America as represented by the Secretary of the Department of Health and Human Services, Washington, D.C.

[21] Appl. No.: 562,013

[22] Filed: Nov. 22, 1995

[51] Int. Cl.[6] .................. C07D 213/70; A61K 31/44
[52] U.S. Cl. .............................. 514/357; 546/335
[58] Field of Search .................. 546/335; 514/357

[56] References Cited

U.S. PATENT DOCUMENTS

| | | | |
|---|---|---|---|
| 3,838,145 | 9/1974 | Ruedi Altermatt | 260/184 |
| 4,051,196 | 9/1977 | Wells et al. | 260/857 |
| 4,568,666 | 2/1986 | McCullagh et al. | 514/20 |
| 5,142,056 | 8/1992 | Kempe et al. | 546/265 |
| 5,180,744 | 1/1993 | Hanson et al. | 514/616 |
| 5,214,129 | 5/1993 | Luly et al. | 530/331 |
| 5,254,724 | 10/1993 | Bergeron, Jr. | 560/312 |
| 5,256,677 | 10/1993 | Sham et al. | 514/351 |
| 5,272,175 | 12/1993 | Hansen, Jr. et al. | 514/487 |
| 5,354,866 | 10/1994 | Kempf et al. | 514/351 |

FOREIGN PATENT DOCUMENTS

| | | |
|---|---|---|
| 0 541 467 A2 | 11/1992 | European Pat. Off. |
| 0580402 | 1/1994 | European Pat. Off. |
| 9118866 | 12/1991 | WIPO |

OTHER PUBLICATIONS

Chemical Abstracts, vol. 124:145557, 1995 Randad et al.
Bone et al., "X-ray Crystal Structure of the HIV Protease Complex with L-700,417, an Inhibitor with Pseudo C2-Symmetry," *Journal of the American Chemical Society*, 113(24), 9382-9384 (1991).
Randad et al., "Symmetry based HIV Protease Inhibitors: Rational Design of 2-Methylbenzamides as Novel P2/P2 Ligands," *Bioorganic and Medical Chemistry Letters*, 5(15), 1707-1712 (1995).

Erickson et al., "Design, Activity, and 2.8 Å Crystal Structure of a $C_2$ Symmetric Inhibitor Complexed to HIV-1 Protease," *Science*, 249:527-533 (Aug. 1990).
Flentge et al., "Symmetry–Based Inhibitors of HIV Protease With High Oral Bioavailability," Abstract, Amer. Chem. Society Mtg. (1994).
Green et al., "Symmetry–Based HIV Protease Inhibitors: Structure–Based Design of P2 Amino Acid Replacements," Abstract, Amer. Chem. Society Mtg. (1993).
Kempf et al., "Antiviral and Pharmacokinetic Properties of $C_2$ Symmetric Inhibitors of the Human Immunodeficiency Virus Type 1 Protease," *Antimicrobial Agents and Chemotherapy*, 35(11):2209-2214 (Nov. 1991).
Kempf et al., "Design of Orally Bioavailable, Symmetry-Based Inhibitors of HIV Protease," *Bioorganic & Medicinal Chemistry*, 2(9):847-858 (1994).
Kempf et al., "Structure–Based, $C_2$ Symmetric Inhibitors of HIV Protease," *Journal of Medicinal Chemistry*, 33(10):2687-2689 (1990).
Kempf et al., "Structure–Based Inhibitors of HIV Protease," Recent Advances in the Chem. of Anti–Infective Agents, Bently et al., eds. Royal Society of Chem., Cambridge (1993) pp. 297-313.
Kempf et al., "Symmetry–Based Inhibitors of HIV Protease. Structure–Activity Studies of Acylated 2,4-Diamino-1, 5-diphenyl-3-hydroxypentane and 2,5-Diamino-1, 6-diphenylhexane-3,4-diol," *J. Med. Chem.* 36:320-330 (1993).
Randad et al., "Symmetry–Based HIV Protease Inhibitors: Rational Design of Hydroxybenzamide as a Novel $P_2$ Replacement," Abstract, AIDS Structure Mtg., NIH (1994).
Chemical Abstracts, vol. 116, No. 21, Abstract 214.912m, May 25, 1992, p. 792.
Chemical Abstracts, vol. 115, No. 5, Abstract 50301r, Aug. 5, 1991, p. 914.

*Primary Examiner*—Zinna Northington Davis
*Attorney, Agent, or Firm*—Leydig, Voit & Mayer, Ltd.

[57] ABSTRACT

The present invention provides novel retroviral agents containing anthranilamide, substituted benzamide, amino acid, and other subunits, a pharmaceutical composition comprising such compound, and a method of using such compounds to treat retroviral infections in mammals, specifically HIV and more specifically HIV-1 and HIV-2, in humans.

9 Claims, No Drawings

RETROVIRAL AGENTS CONTAINING ANTHRANILAMIDE, SUBSTITUTED BENZAMIDE AND OTHER SUBUNITS, AND METHODS OF USING SAME

TECHNICAL FIELD OF THE INVENTION

This invention relates to 2,5-diamino-3,4-disubstituted-1, 6-diphenylhexane (DAD) isosteres comprising novel, nonpeptidic and achiral subunits and, more particularly, to DAD isosteres comprising anthranilamide, substituted benzamide and other subunits. The DAD isosteres of this invention may include amino acid subunits. This invention also relates to a pharmaceutical composition comprising such compounds, a method of using such compounds to treat retroviral infections in mammals, and a method of using such compounds in antiretroviral activity assays.

BACKGROUND OF THE INVENTION

Acquired immune deficiency syndrome (AIDS) is a fatal disease, reported cases of which have increased dramatically within the past several years. Estimates of reported cases in the very near future also continue to rise dramatically. Consequently, there is a great need to develop drugs and vaccines to combat AIDS.

The AIDS virus was first identified in 1983. It has been known by several names and acronyms. It is the third known T-lymphocyte virus (HTLV-III), and it has the capacity to replicate within cells of the immune system, causing profound cell destruction. The AIDS virus is a retrovirus, a virus that uses reverse transcriptase during replication. This particular retrovirus is also known as lymphadenopathy-associated virus (LAV), AIDS-related virus (ARV) and, most recently, as human immunodeficiency virus (HIV). Two distinct families of HIV have been described to date, namely HIV-1 and HIV-2. The acronym HIV will be used herein to refer to HIV, viruses generically.

Specifically, HIV is known to exert a profound cytopathic effect on the CD4+ helper/inducer T-cells, thereby severely compromising the immune system. HIV infection also results in neurological deterioration and, ultimately, in the death of the infected individual.

The field of viral chemotherapeutics has developed in response to the need for agents effective against retroviruses, in particular HIV. There are many ways in which an agent can exhibit anti-retroviral activity. For example, HIV requires at least four viral proteins for replication: reverse transcriptase (RT), protease (PR), transactivator protein (TAT), and regulator of virion-protein expression (REV). Accordingly, viral replication theoretically could be inhibited through inhibition of any one or all of the proteins involved in viral replication.

The PR processes polyprotein precursors into viral structural proteins and replicative enzymes. This processing is essential for the assembly and maturation of fully infectious virions. Accordingly, the design of PR inhibitors is an important therapeutic goal in the treatment of AIDS.

Anti-retroviral agents, such as 3'-azido-2',3'-dideoxythymidine (AZT), 2',3'-dideoxycytidine (ddC), and 2',3'-dideoxyinosine (ddI) are known to inhibit RT. There also exist antiviral agents that inhibit TAT.

Nucleoside derivatives, such as AZT, are the only clinically active agents that are currently available for antiviral therapy. Although very useful, the utility of AZT and related compounds is limited by toxicity and insufficient therapeutic indices for fully adequate therapy.

Numerous classes of potent peptidic inhibitors of PR have been designed using the natural cleavage site of the precursor polyproteins as a starting point. These inhibitors typically are peptide substrate analogs in which the scissile $P_1$—$P_1$, amide bond has been replaced by a nonhydrolyzable isostere with tetrahedral geometry (Moore et al., *Perspect. Drug Dis. Design*, 1, 85 (1993); Tomasselli et al., *Int. J. Chem. Biotechnology*, 6 (1991); Huff, *J. Med. Chem.*, 34, 2305 (1991); Norbeck et al., *Ann. Reports Med. Chem.*, 26, 141 (1991); Meek, *J. Enzyme Inhibition*, 6, 65 (1992)). Although these inhibitors are effective in preventing the retroviral PR from functioning, the inhibitors suffer from some distinct disadvantages. Generally, peptidomimetics often make poor drugs due to their potential adverse pharmacological properties, i.e., poor oral absorption, poor stability and rapid metabolism (Plattner et al., *Drug Discovery Technologies*, Clark et al., eds., Ellish Horwood, Chichester, England (1990)). Furthermore, since the active site of the PR is hindered, i.e., has reduced accessibility as compared to the remainder of the PR, the ability of the inhibitors to access and bind in the active site of the PR is impaired, and those that do bind are generally poorly water-soluble, causing distinct problems in drug delivery.

The design of HIV-1 protease inhibitors based on the transition state mimetic concept has led to the generation of a variety of peptide derivatives highly active against viral replication in vitro (Erickson et al., *Science;* 249, 527–533 (1990); Kramer et al., *Science*, 231, 1580–1584 (1986); McQuade et al., *Science*, 247, 454–456 (1990); Meek et al., *Nature (London)*, 343, 90–92 (1990); Roberts et al., *Science*, 248, 358–361 (1990)). These active agents contain a non-hydrolyzable, dipeptide isostere such as hydroxyethylene (McQuade et al., supra; Meek et al., *Nature (London)*, 343, 90–92 (1990); Vacca et al., *J. Med. Chem.*, 34, 1225–1228 (1991)) or hydroxyethylamine (Rich et al., *J. Med. Chem.*, 33, 1285–1288 (1990); Roberts et al., *Science*, 248, 358–361 (1990)) as an active moiety which mimics the putative transition state of the aspartic protease-catalyzed reaction. Twofold ($C_2$) symmetric inhibitors of HIV protease represent another class of potent HIV protease inhibitors which were created by Erickson et al. on the basis of the three-dimensional symmetry of the enzyme active site (Erickson et al., supra). A-77003 and other compounds designed on the $C_2$ symmetry are undergoing clinical trials in humans (Kempf et al., *Antimicrob. Agents Chemother.*, 35, 2209 (1991); Kempf et al., U.S. Pat. No. 5,142,056; Kempf et al., *J.Med.Chem* 1993, 36, 320–330).

Nonpeptidic inhibitors of HIV-1 protease have been reported recently. Kalish et al., *Bioorganic & Medicinal Chemistry Letters*, Vol. 5, No. 7, pp. 727–732, 1995.

The use of HIV protease inhibitors in combination with agents that have different antiretroviral mechanisms (e.g., AZT, ddI and ddT) also has been described. For example, synergism against HIV-1 has been observed between certain $C_2$ symmetric HIV inhibitors and AZT (Kageyama et al., *Antimicrob. Agents Chemother.*, 36, 926–933 (1992)).

The usefulness of currently available HIV protease inhibitors in the treatment of AIDS has been limited by relatively short plasma half-life, poor oral bioavailability, and the technical difficulty of scale-up synthesis (Meek et al., *J. Enzyme Inhibition*, 6, 65–98 (1992)). It has also been reported recently that the effectiveness of HIV protease inhibitors that have an affinity for and/or bind to α-1 acid glycoprotein is impaired for a given dosage because of the antagonist action of the α-1 acid glycoprotein, a protein whose concentration is known to be elevated in AIDS patients. Bilello J. A. et al., *Journal of Infectious Diseases,*

1995, 71, 546–551. There remains an urgent need, therefore, for retroviral protease inhibitors that do not suffer from the disadvantages of currently available retroviral protease inhibitors as well as effective methods of treating retroviral infection, in particular HIV infection, involving the administration of novel antiretroviral agents alone and in combination with other antiretroviral therapies.

Accordingly, it is an object of the present invention to provide antiretroviral compounds, specifically retroviral protease inhibitors, that are resistant to viral and mammalian protease degradation and which, therefore, have improved plasma half-life and oral bioavailability. It is a further object of the invention to provide retroviral protein inhibitors for which α-1 acid glycoprotein is not an antagonist. It is a related object of the present invention to provide a method of treating retroviral infection in a mammal, especially HIV and HIV-1 and HIV-2 in a human, which involves the administration of one or more of the antiretroviral compounds of the present invention alone or in combination with one or more other, currently available, antiretroviral therapies. Accordingly, it is also an object of the present invention to provide pharmaceutical compositions comprising the antiretroviral compounds. Another object of the present invention is to provide a method of using such compounds to assay new compounds for antiretroviral activity. These and other objects and advantages of the present invention, as well as additional inventive features, will be apparent from the description of the invention provided herein.

BRIEF SUMMARY OF THE INVENTION

The present invention provides symmetric and asymmetric antiretroviral compounds which are protein inhibitors. The compounds of the present invention are DAD isosteres with achiral, nonpeptidic anthranilimide, substituted benzamide, sulfonamide and other subunits. The DAD isosteres of this invention may include amino acid subunits. The novel compounds of this invention have the structure:

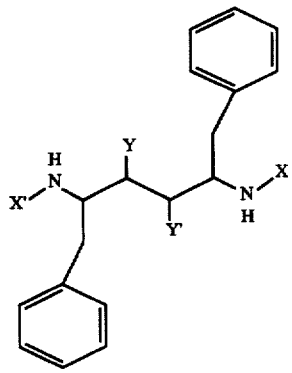

The stereochemistry of each of the benzyl groups on the carbon atoms adjacent to the carbon atoms with the Y and Y' substituents is R or S. Y and Y' are the same or different and are R-hydroxyl, S-hydroxyl or hydrogen. X and X' may be the same or different, depending on the anthranilimide, substituted benzamide, amino acid or other subunit selected for the compound. X and X' have the formula:

wherein Z is phenyl, substituted phenyl, analine, N-substituted analine, analine in which the aromatic ring is substituted, —OR' wherein R' is furanyl, tert-butyl, benzyl, substituted benzyl, $CH_2$-pyridinyl, or $CH_2$ thiazolyl; or an amino acid residue or N-protected amino acid residue.

The present invention also provides a pharmaceutical composition comprising one or more of the above-described compounds alone or in combination with one or more other currently available antiretroviral compounds. A method of treating a retroviral infection in a mammal, specifically HIV and more specifically HIV-1 and HIV-2, in a human, is further provided wherein a compound in accordance with the invention, is administered alone or in combination with one or more other currently available antiretroviral therapies. Also further provided are a method of using such compounds to assay new compounds for antiretroviral activity.

DETAILED DESCRIPTION OF THE INVENTION

The present invention provides DAD isosteres with anthranilamide, substituted benzamide, sulfonamide, amino acid and other subunits. The compounds are antiretroviral protease inhibitors. In particular, the compounds inhibit the protease of HIV, more specifically the protease of HIV-1 and HIV-2. The compounds are characteristically different from currently available antiretroviral protease inhibitors. Such differences include, among others, resistance to mammalian and viral protease degradation, which is believed to be due to structural differences, namely the novel, nonpeptidic and achiral anthranilamide, substituted benzamide, sulfonamide and other subunits that have been introduced into the DAD isosteres. Such differences, such as resistance to protease degradation, result in improved plasma half-life and oral bioavailability. It has also been observed in in vitro studies that the activity of at least one of the compounds (DN-14) is not affected by the presence of α-1 acid glycoprotein.

The compounds provided by the present invention have the formula:

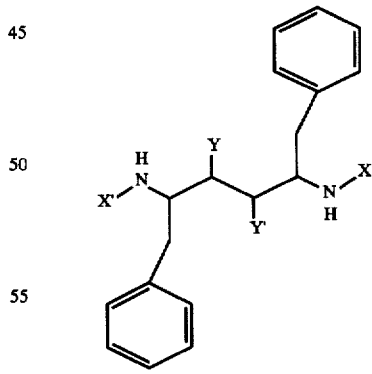

wherein the stereochemistry of each of the benzyl groups on the carbon atoms adjacent to the carbon atoms with the Y and Y' substituents is R or S. Y and Y' are the same or different and are R-hydroxyl, S-hydroxyl or hydrogen; and In the above formula, X and X', may be the same or different and, are selected from the following five groups.

X and X' can have the formula:

wherein Q is aniline, an aromatic ring-substituted aniline or N-substituted analine. For Q, both the aromatic ring and the nitrogen may be substituted. In the aromatic ring-substituted aniline, the substitutent on the phenyl ring is one or more of hydroxyl, $C_1$–$C_4$ or halogen. In the N-substituted aniline, the substituent on the aniline nitrogen is —COO($CH_2$)$_p$R, wherein p is 0 to 4 and R is phenyl, pyridinyl, thiazolyl, or morpholinyl.

X and X' can also have the formula:

wherein R' is furanyl, tert-butyl, or ($CH_2$)R". R" is pyridinyl, thiazolyl, morpholinyl, phenyl, or substituted phenyl. For the substituted phenyl, the phenyl substitutent is one or more of halogen, hydroxyl, amino or $C_1$–$C_4$ alkyl.

X and X' can have the formula:

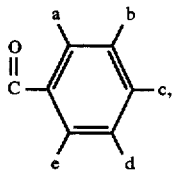

wherein a–e are the same or different. Here, a–e are hydrogen, hydroxyl, $C_1$–$C_4$ alkyl, halogen, or amino.

X and X' can have the formula:

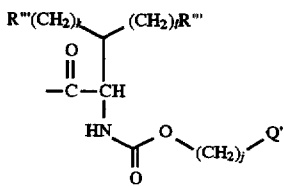

wherein j is 0 to 2, k is 1 to 4, and l is 0 to 4. Q' is phenyl, pyridinyl, thiazolyl, morpholinyl, or substituted phenyl. The substituents on the substituted phenyl are one or more of hydroxyl, $C_1$–$C_4$ alkyl, halogen or amino. R'" is hydrogen, hydroxyl, halogen, —COOH, —$CONH_2$, O—$C_{1-4}$ alkyl, SH, S—$C_{1-4}$ alkyl or S-aryl.

X and X' can also be an N-protected amino acid residue. Preferably the amino acid residue is a residue of asparagine, histidine, methionine, phenylalanine, threonine, and O-methyl threonine. The N-protecting group on the amino acid residue has the formula:

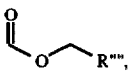

wherein R"" is phenyl, pyridinyl, thiazolyl or morpholinyl.

Accordingly, the present invention provides symmetric and asymmetric 2,5-diamino-3,4-disubstituted-1,6-diphenylhexane (DAD) isosteres comprising anthranilamide, substituted benzamide, sulfonamide, amino acid and other subunits such as, by way of example, O-tert-butyl, O-furanyl and the like. The asymmetric compounds can be asymmetric with respect to X and X' or with respect to the substituents a–e that are present on X and X', in particular with respect to substituted amino groups, for example. Representative compounds are presented in Tables I–III. The substituents on these compounds, in particular on the substituted amino groups, may be further modified as necessary to affect activity and ease the preparation of a given pharmaceutical formulation, for example.

Preferred compounds of the present invention include the following compounds:

(a) (2S,3R,4S,5S)-2-[N-(N-benzyloxycarbonyl)valinyl) amino]-5-[N-[N-((2-pyridinylmethoxy)carbonyl) anthranilyl]amino]-3,4-dihydroxy-1,6-diphenyl hexane (DN-14).

(b) (2S,3R,4S,5S)-2-[N-(N-(2-pyridinylmethoxy)valinyl) amino]-5-[N-[N-((2-pyridinylmethoxy)carbonyl) anthranilyl]amino]-3,4-dihydroxy-1,6-diphenyl hexane (LL-73).

(c) (2S,3S,5S)-2-[N-(N-(2-pyridinylmethoxy)valinyl) amino]-5-[N-[N-((2-pyridinylmethoxy)carbonyl) anthranilyl]amino]-1,6-diphenyl-3-hydroxy hexane (LL-75).

(d) (2S,3S,5S)-2-[N-[(3-hydroxy-2-methylphenyl) carbonyl]amino]-5-[N-[N-[(2-pyridinylmethoxy) carbonyl]anthranilyl]amino]-1,6-diphenyl-3-hydroxy hexane (LL-82).

(e) (2S,3S,5S)-5-[N-[N-((2-pyridinylmethoxy)carbonyl) anthranilyl]amino]2-[N-((3-S-(tetrahydrofuranyl)oxy) carbonyl)amino]-1,6-diphenyl-3-hydroxy hexane (LL-101).

(f) (2S,3S,5S)-2-[N-[(3-hydroxy-2-methylphenyl) carbonyl]amino]-5-[N-(3-aminophenyl)carbonyl] amino-1,6-diphenyl-3-hydroxy hexane (AN-96).

(g) (2S,3S,5S)-2-[N-[(3-hydroxy-2-methylphenyl) carbonyl]amino]-5-[N-(3-S-(tetrahydrofuranyl)oxy) carbonyl]amino]-1,6-diphenyl-3-hydroxy hexane (AN-98).

Especially preferred is compound DN-14.

The compounds of the present invention may be synthesized by methods known to those of skill in the art. For example, DAD (Kempf et al., J. Org. Chem., 57, 5692–5700 (1992); Stuk et al., J. Org. Chem., 59, 4040–4041 (1994)) can be reacted with suitably substituted acid or acid chloride in methylene chloride, toluene, preferably dimethylformamide at ambient temperature, i.e., room temperature. The acids also can be condensed with DAD using standard peptide coupling agents (Bodanszky et al., In The Practice of Peptide Synthesis, Springer-Verlag, New York, N.Y. (1984)). Suitable methods of synthesis are described in Examples 1–11. The asymmetric compounds of the present invention also may be synthesized in accordance with the present inventive method as described in Examples 2–11 and in Schemes II–V. The reaction schemes may be tailored for specific compound, as for example the use of various blocking groups or the like as shown in Example 8 wherein fluorenylmethyl is used, although it is not shown in the reaction schemes set forth. It will be appreciated by those skilled in the art that the various compounds described in Tables I–III below can all be prepared readily by using the synthesis procedures set forth in the schemes and in the Examples by appropriate variation of the chemical reactants, and that other compounds not specifically exemplified may be so prepared.

Also provided by the present invention is a pharmaceutical composition comprising a retroviral proliferation-inhibiting, particularly a HIV proliferation-inhibiting and more particularly a HIV-1 and/or HIV-2 proliferation-inhibiting, effective amount of one or more of a compound as described above, alone or in combination with one or more of a currently available anti-retroviral compound, such as AZT, ddI, ddC, D4T, lamivudine or 3TC, in a pharmaceutically acceptable carrier. Pharmaceutically acceptable carriers are well-known to those who are skilled in the art. The choice of carrier will be determined in part by the particular composition, as well as by the particular method used to administer the composition. Accordingly, there is a wide variety of suitable formulations of the pharmaceutical composition of the present invention.

Formulations suitable for oral administration can consist of (a) liquid solutions, such as an effective amount of the polymer-bound composition dissolved in diluents, such as water or saline, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

Accordingly, the present invention also provides a method of treating a retroviral, particularly a HIV infection and more particularly a HIV-1 or HIV-2 infection, in a mammal, particularly a human, wherein a retroviral proliferation-inhibiting amount of one or more of the present inventive compounds, alone or in combination with one or more other antiretroviral therapies or compounds, such as AZT, ddI, ddC, D4T, lamivudine or 3TC, is administered to a mammal infected with a retrovirus, particularly HIV and more particularly HIV-1 or HIV-2, the proliferation of which is inhibited by a retroviral proliferation-inhibiting amount of a present inventive compound. The dose administered to an animal, particularly a human, in the context of the present invention should be sufficient to effect a therapeutic response in the animal over a reasonable time frame. The dose will be determined by the strength of the particular composition employed and the condition of the animal, as well as the body weight of the animal to be treated. The size of the dose also will be determined by the existence, nature, and extent of any adverse side-effects that might accompany the administration of a particular composition. What constitutes a retroviral proliferation-inhibiting amount, particularly a HIV proliferation-inhibiting amount, and more particularly a HIV-1 or HIV-2 proliferation-inhibiting amount, of one or more compounds of the present invention, alone or in combination with one or more other currently available antiretroviral compounds can be determined, in part, by use of one or more of the assays described herein. Similarly, whether or not a given retrovirus is inhibited by a retroviral proliferation-inhibiting amount of a compound of the present invention can be determined through the use of one or more of the assays described herein or in the scientific literature or as known to one of ordinary skill in the art.

One skilled in the art will appreciate that suitable methods of administering the compounds and pharmaceutical compositions of the present invention to an animal are available, and, although more than one route can be used to administer a particular composition, a particular route can provide a more immediate and more effective reaction than another route. One or more of the present inventive compounds, alone or in combination with one or more other antiretroviral therapies or compounds, can be administered to a mammal, in particular a human, as a prophylactic method to prevent retroviral, particularly HIV and more particularly HIV-1 or HIV-2, infection.

In addition, compounds of the present invention, such as, demonstrate good fluorescence. The determination of which compounds of the present invention fluoresce can be done in accordance with methods well-known to those of ordinary skill in the art. Such fluorescence can be used to assay for antiviral activity of newly discovered compounds. For example, a fluorescent compound of the present invention can be used as a standard in an antiviral activity assay. The fluorescence of the compound can be measured in the absence and presence of a viral enzyme, such as a retroviral enzyme, in particular a retroviral protease, e.g., an HIV protease, in vitro. A test compound can then be added to the test system comprising the fluorescent compound and the enzyme. The decreased fluorescence of the fluorescent compound of the present invention in the absence and presence of the test compound can be measured and quantitated as a measure of the antiviral activity of the test compound.

The following examples further illustrate the present invention, but do not limit the scope thereof.

EXAMPLE 1

This example describes the synthesis of DAD isosteres with benzamide and anthranilamide subunits.

Compounds were synthesized as shown in Scheme I. The inhibitor core unit 3 (2S,3R,4S,5S-2,5-diamino-1,6-diphenyl-3,4-hexanediol) was synthesized by McMurray coupling of natural Boc-phenylalaninal (Kempf et al. (1992), supra). The 2,5-diamino compound 3 (X=OH) was condensed with suitably substituted benzoic acid using the 1-H-benzatriol-1-yl-1,1,3,3-tetramethyl-ammonium tetrafluoroborate (TBTU)/1-hydroxybenzotriazole (HOBt)/ diisopropylethyl amine (DIPEA) method to provide compounds with benzamide subunits. The 2,5-diamino compound 3 (where, in Scheme I, X=OH) was condensed with suitably substituted N-acyl anthranilic acid using the TBTU/HOBt/DIPEA method to provide compounds with anthranilamide subunits. The N-acyl anthranilamides were prepared by reaction of anthranilic acid with corresponding acid chloride. In accordance with Kempf, the structures of all compounds prepared were established by proton nuclear magnetic resonance ($^1$H NMR) spectroscopy and mass spectral (FAB and/or high resolution mass spectra (HRMS)) analysis. $^1$H NMR spectra were recorded on a Varian XL-200 and 500 MHz spectrometer; data were reported in δ ppm scale relative to TMS. FAB spectra and HRMS were recorded on a VG ZAB-2F spectrometer (Manchester, England) and on a VG70-250 spectrometer, respectively.

-continued
SCHEME 1.

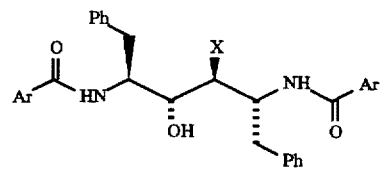

SCHEME 1.

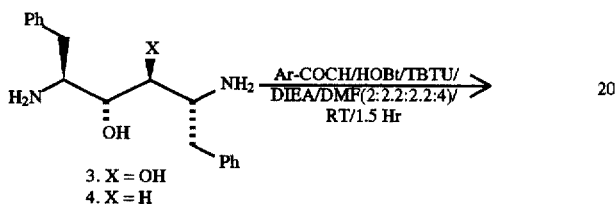

3. X = OH
4. X = H

SCHEME II

ASYMMETRIC COMPOUNDS: GENERAL SCHEME FOR SYNTHESIS OF DN SERIES

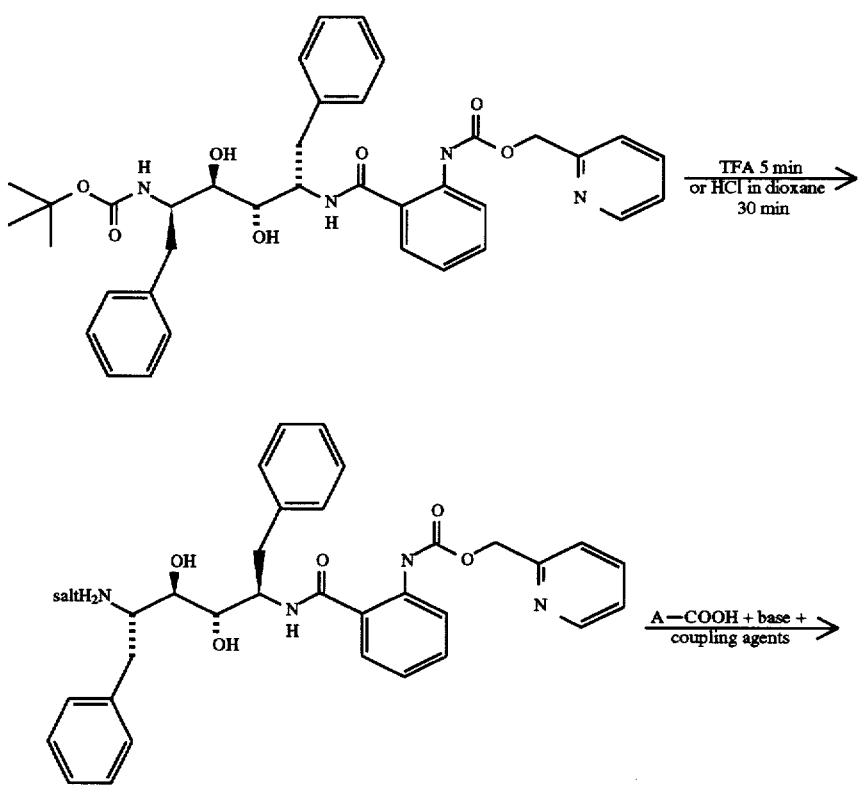

-continued
SCHEME II
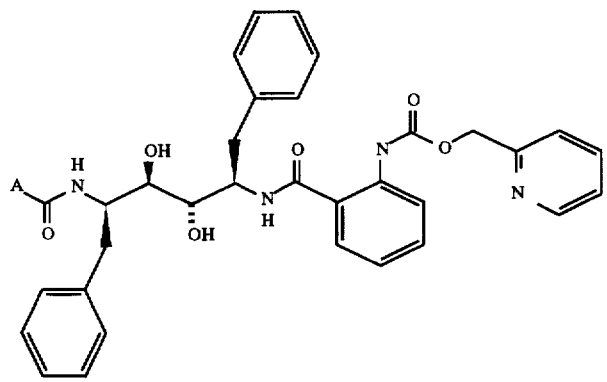
SCHEME III
ASYMMETRIC COMPOUNDS:
GENERAL SCHEME FOR SYNTHESIS OF ND SERIES
-continued
SCHEME III
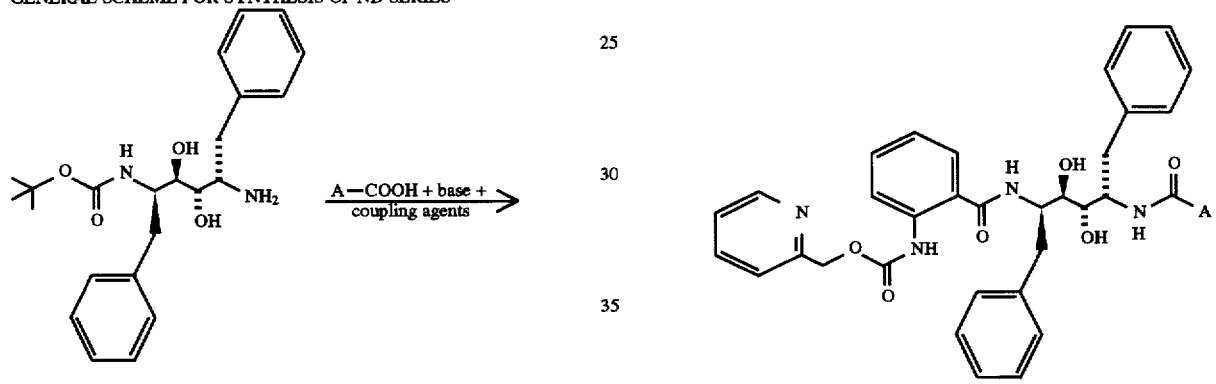
ND-4 when A is 3-hydroxyphenyl
SCHEME IV
ASYMMETRIC COMPOUNDS: GENERAL SYNTHETIC SCHEME FOR DESHYDROXY COMPOUNDS.
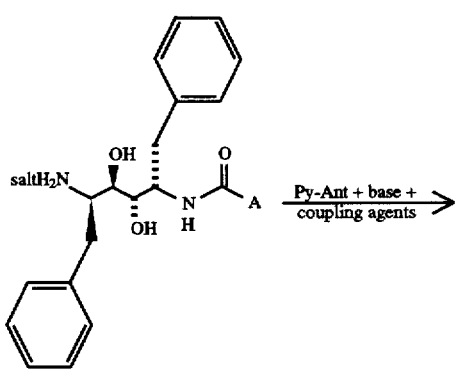
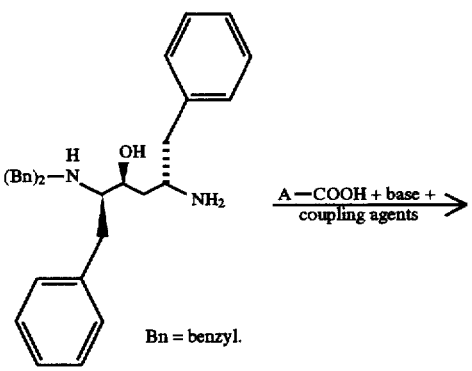
Bn = benzyl.

13
-continued
SCHEME IV
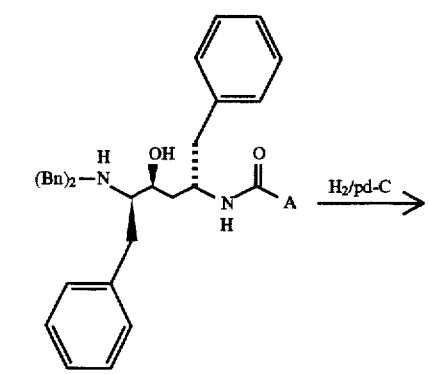
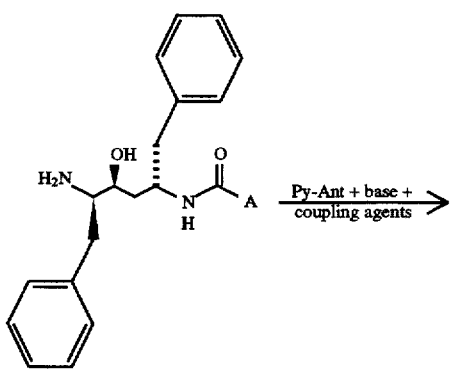
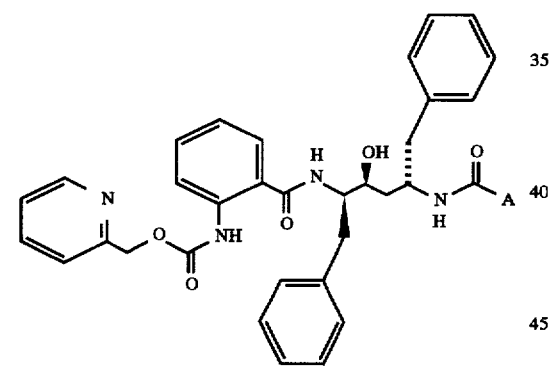
SCHEME V
ASYMMETRIC COMPOUNDS: GENERAL SYNTHETIC SCHEME FOR DESHYDROXY COMPOUNDS.
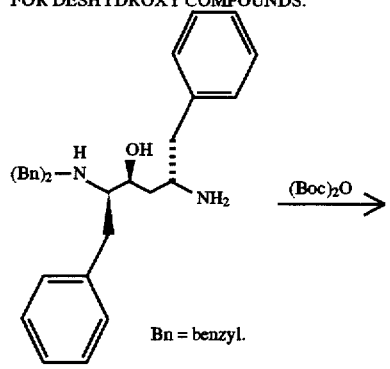
Bn = benzyl.
14
-continued
SCHEME V
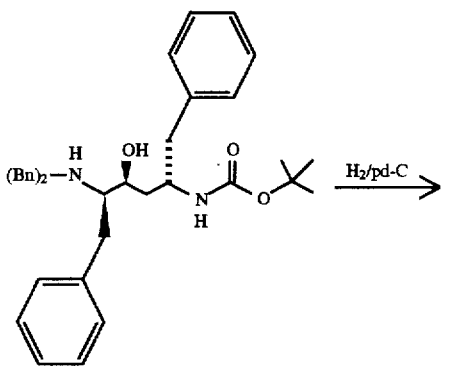
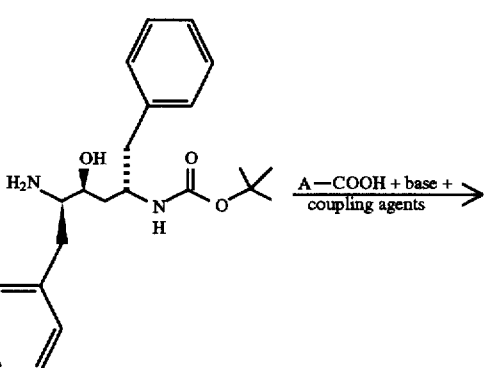
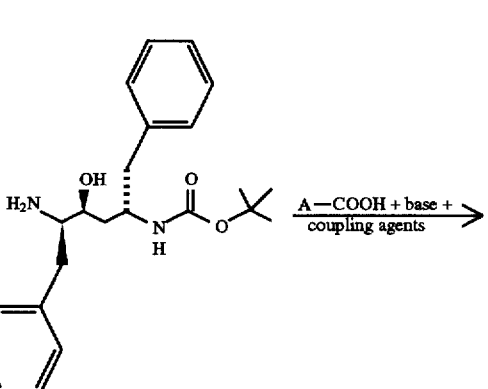
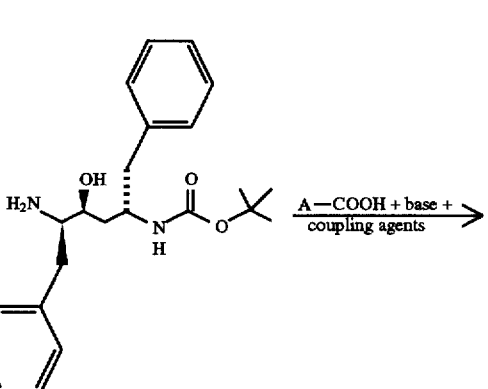

-continued
SCHEME V
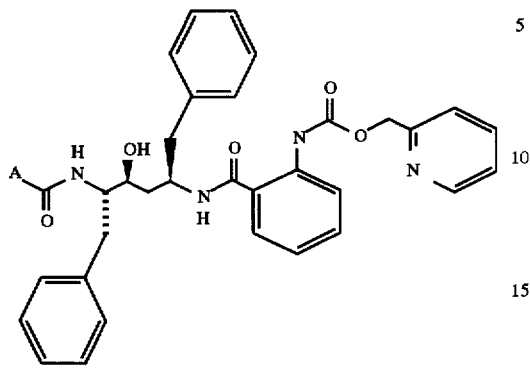
EXAMPLE 2
This example describes the synthesis of [2S,3R,4S,5S]-2-[N-[tert-butyloxy)carbonyl]amino]-5-[((N-[N-2-pyridinylmethyloxy)carbonyl]anthranyl)amino]-3,4-dihydroxy-1,6-diphenylhexane (DN-11).
DN-11 was synthesized according to the following reaction scheme:
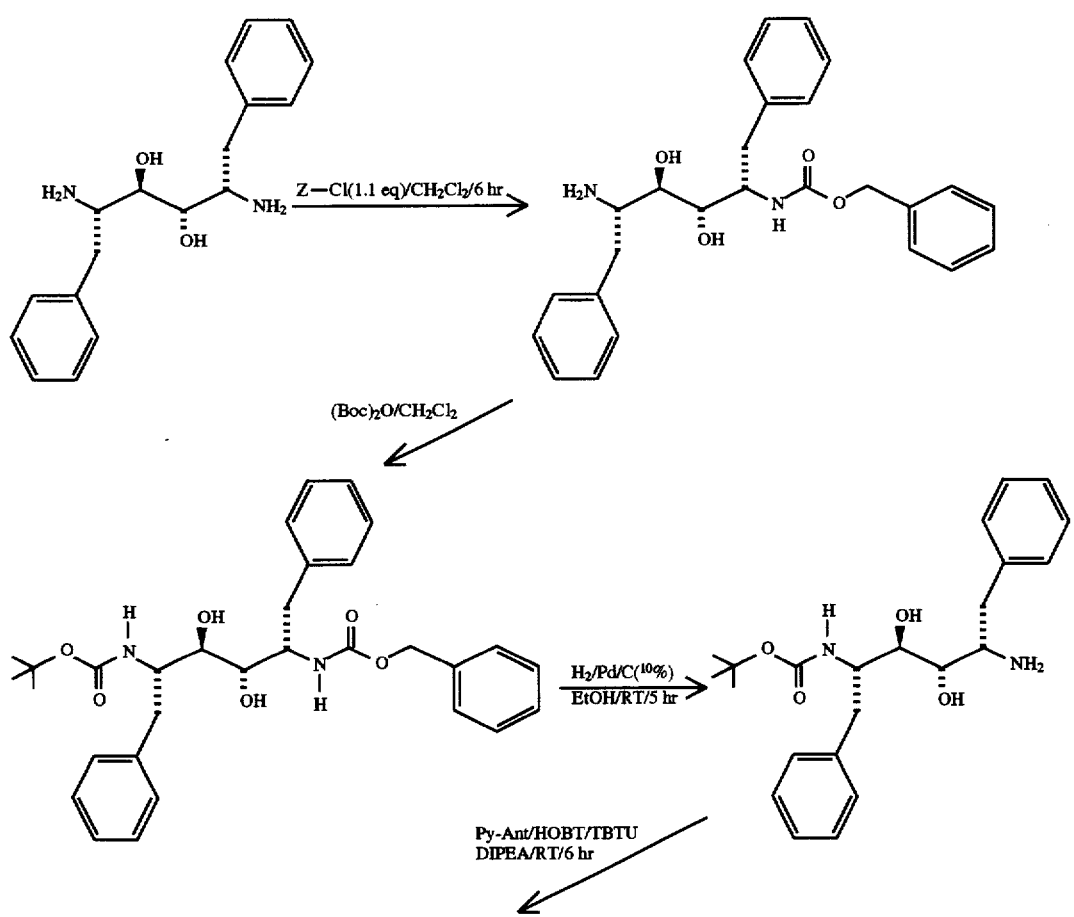

-continued

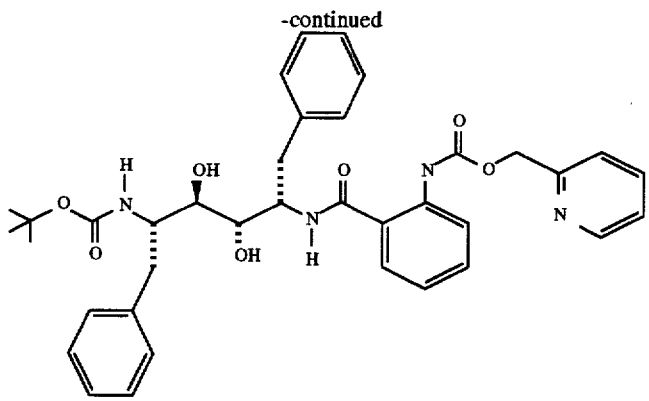

A solution of (2S,3R,4S,5S)-2-amino-5-(N-benzyloxycarbonylamino)-3,4-dihydroxy-1,6-diphenylhexane (250 mg, 0.575 mmol) and (Boc)$_2$O (138 mg, 0.63 mmol) in methylene chloride (15 ml) was stirred at room temperature for 24 hr. The volatiles were removed under vacuum, and the residue was diluted with ethyl acetate, washed sequentially with 10% solution of KHSO$_4$ water, and aqueous NaHCO$_3$, and dried over MgSO$_4$. The yield of product was 308 mg. The compound was crystallized from the solvent system EtOAc-hexanes 1:2. The yield of crystallized product was 270 mg (88%).

A continuous stream of hydrogen was bubbled through a solution of (2S,3R,4S,5S)-2-(N-tert-butyloxycarbonyl amino)-5-(N-benzyloxycarbonylamino)-3,4-dihydroxy-1,6-diphenylhexane (500 mg) in ethanol (80 ml) containing 10% Pd on carbon (40 mg) for 5 hr (Bodanszky et al. (1984), supra, at page 153). The reaction mixture was filtered through celite and concentrated in vacuum to provide 316 mg of (2S,3R,4S,5S)-2-(N-tert-butyloxycarbonylamino)-5-amino-3,4-dihydroxy-1,6-diphenylhexane (Boc-DAD).

A solution of (N-2-pyridinylmethyloxy)carbonyl) anthranilic acid (Py-Ant, 30 mg, 0.11 mmol), Boc-DAD (40 mg, 0.1 mmol), HOBT (16 mg, 0.1 mmol), TBTU (32 mg, 0.1 mmol), in DMF (20 ml) was treated with DIPEA (26 mg, 35 µl, 0.2 mmol) and then stirred at room temperature for 6 hr. The solvents were removed under vacuum, and the residue was diluted with ethyl acetate, washed sequentially with a 10% solution of KHSO$_4$, water and aqueous NaHCO$_3$, and dried over MgSO$_4$. Yield: 65 mg. The compound was crystallized from the solvent system EtOAc-hexanes (1:1). The yield after crystallization was 26 mg. MS(M+Na) 677; $^1$H NMR (methanol-d$_4$),δ1.231 (m, 9H), 2.59–2.64 (m, 2H), 2.89–2.93 (m, 1H),2.97–3.07 (m, 2H), 3.59–3.67 (m, 2H), 4.15–4.19 (m, 1H), 4.66–4.69 (m, 2H), 5.21–5.29 (m, 2H), 7.06–7.09 (m, 1H), 7.11–7.14 (m, 2H), 7.17–7.25 (m, 7H), 7.30–7.32 (m, 2H), 7.35–7.37 (m, 1H), 7.41–7.45 (m, 1H), 7.51–7.54 (m, 2H), 7.84–7.88 (m, 1H), 8.111 (d, J=4.6 Hz, 1H), 8.51–8.52 (m, 2H). K$_i$=0.4 nM.

In the following examples, all melting points were recorded on a Electrothermal Digital Melting Point Apparatus (Model IA9200) and are uncorrected. Proton nuclear magnetic resonance ($^1$H NMR) spectra were recorded on a Varian XL-300 or VXR-500S MHz spectrometer. $^1$H NMR spectral data are reported in d ppm scale relative to TMS. High resolution mass spectra were recorded on a VG70-250 and FAB mass spectra on a VG ZAB-2F (Manchester, England) mass spectrometer. Flash chromatography was performed on silica gel (230–400 mesh, E. Merck). HPLC analyses were carried out using a Hewlett Packard 1050 chromatograph using a methanol/water (0.05% TFA) mixtures as mobile phase (gradient 50–100% of methanol during 30 min.) on analytical: YMC-Pack ODS-AQ (C18) (250×4.6 mm, S-5 µm, 120 Å) reverse phase column. Thin-layer chromatography was performed on silica gel F-254 plates (0.25; Whatman) and visualized using sulfuric acid or chlorine or ninhidrin/TDM (4,4'-tetramethyldiaminodiphenylethane) and UV methods.

EXAMPLE 3

This example illustrates the synthesis of (2S,3S,5S)-2-[N-[(3-hydroxy-2-methylphenyl)carbonyl]amino]-5-[N-(tert-butyloxycarbonyl)amino]-1,6-diphenyl-3-hydroxy hexane (RS-208).

The compound (2S,3S,5S)-5-[N-(tert-butyloxycarbonyl) amino]-2-N-dibenzylamino-1,6-diphenyl-3-hydroxy hexane (RS-215) was prepared as follows. A solution of (2S,3S,5S)-5-amino-2-dibenzylamino-1,6-diphenyl-3-hydroxy hexane (RS-214, 51 g, 0.11 mol), and tert-butyldicarbonate (28.3 g, 0.13 mol) in methylene chloride (500 ml) was stirred at room temperature for 12 h. Solvents were evaporated and residue was diluted with ethyl acetate and sequentially washed with aqueous NaHCO$_3$ and brine, then dried on MgSO$_4$ and concentrated in vacuo. (Yield 69 g) The thick liquid product was purified on flash chromatography using hexane—ethyl acetate mixtures (9.6:4–9:1). Yield of pure product after chromatography 47 g (76%); TLC [R$_f$=0.65 (ethyl acetate:hexane, 2:8)]; HPLC rt (retention time)=18.8 min.; MS m/z 566 (M+H)$^+$; $^1$H NMR (CDCl$_3$); 500 MHz; d: 1.40 (s, 9H), 1.43–1.53 (m, 2H), 2.57 (dd, J=14.3; 6.6 Hz, 1H), 2.67 (dd, J=13.4; 6.8 Hz, 1H), 2.76–2.80 (m, 2H), 3.04 (dd, J=14.4; 5.9 Hz, 1H) 3.36 (d, J=13.4 Hz, 2H), 3.59 (dt, J=8.5; 2.0 Hz, 1H), 3.76–3.82 (m, 1H), 3.89 (d, 1H, J=13.3 Hz), 4.34 (s, 1H), 4.86 (bs, 1H), 7.02–7.04 (m, 2H), 7.09–7.11 (m, 2H), 7.15–7.31 (m, 16H).

The compound (2S,3S,5S)-2-amino-5-[N-(tert-butyloxycarbonyl)amino]-1,6-diphenyl-3-hydroxy-2 hexane (RS-216) was prepared from RS-215 as follows. A solution of (2S,3S,5S)-5-[N-(tert-butyloxycarbonyl)amino]-2-N-dibenzylamino-1,6-diphenyl-3-hydroxy hexane (RS-215, 49 g, 0.09 mol), aqueous ammonium formate (34 g in 52 ml of water), 5% palladium on carbon (10 g) in methanol (700 ml) was heated to reflux for 6 h. The cooled suspension was filtered through the filtering agent Celite 521, washed with methanol and concentrated in vacuo. The residue was dissolved in ethyl acetate (300 ml) and was washed sequentially with 1N NaOH (50 ml), brine, then dried over K$_2$CO$_3$ and evaporated to yield 31 g (89%) white solid product; Yield 31 g (89%); mp=118°–119° C.; TLC [Rf=0.50 (chloroform:methanol, 1:1)]; HPLC rt=14.4 min.; MS m/z 385 (M+H)⁺; ¹H NMR (CDCl₃/CD₃OD), 500 MHz; d: 1.41 (s, 9H), 1.53–1.60 (m, 1H), 1.68–1.74 (m, 1H), 2.47 (dd, J=13.4; =9.4 Hz, 1H), 2.79 (dd, J=13.4; 6.9 Hz, 1H), 2.82 (d, J=4.5 Hz, 1H), 2.84 (d, J=4.5 Hz, 1H), 2.86–2.91 (m, 1H), 3.46–3.50 (m, 1H), 3.92–3.98 (m, 1H), 4.82–4.88 (m, 1H), 7.14–7.31 (m, 10H).

The compound (2S,3S,5S)-2-[N-[(3-hydroxy-2-methylphenyl)carbonyl]amino]-5-[N-(tert-butyloxycarbonyl)amino]-1,6-diphenyl-3-hydroxy hexane (RS-208) was prepared from RS-216. A solution of (2S,3S,5S)-2-amino-5-[N-(tert-butyloxycarbonyl)amino]-1,6-diphenyl-3-hydroxy hexane (RS-216, 1.1 g, 2.86 mmol), 3-hydroxy-2-methyl-benzoic acid (0.478 g, 3.2 mmol), O-(1H-benzotriazol-1-yl)-N,N,N',N'-tetramethyluronium tetrafluoroborate (TBTU, 1.02 g, 3.2 mmol), 1-hydroxybenzotriazole hydrate (HOBT, 0.919 g, 6.0 mmol) and diisopropylethylamine (DIPEA, 103 ml, 6.0 mmol) in dimethylformamide (DMF, 30 ml) was stirred at room temperature for 2 h. After addition of aminoethyl morpholine (50 ml) the solvents were removed under vacuum and the residue was diluted with ethyl acetate and washed sequentially with aqueous NaHCO₃, aqueous KHSO₄, brine, then dried on Na₂SO₄, and concentrated in vacuo. Solid was suspended in ethyl acetate, filtered and residue was washed with ethyl acetate. Crystallization from ethyl acetate:methanol:hexane (1:0.2:1.5) provided 1.4 g (94%) of white solid; mp=162°–163° C.; TLC [R_f=0.75 (ethyl acetate:hexane, 7:3)]; HPLC rt=19.5 min; MS m/z 519 (M+H)⁺; ¹H NMR.

EXAMPLE 4

The compound (2S,3S,5S)-2-[N-[(3-hydroxy-2-methylphenyl)carbonyl]amino]-5-[N-[(3-pyridinyl methoxy)carbonyl]amino]-1,6-diphenyl-3-hydroxy hexane (AN-92) was prepared as follows. A solution of (2S,3S,5S)-5-Amino-2-[N-[(3-hydroxy-2-methylphenyl)carbonyl]amino]-1,6-diphenyl-3-hydroxy hexane hydrochloride salt (AN-87, 40.9 mg, 0.09 mmol) and O-(3-pyridinyl methyl)-O'-(4-nitrophenyl)carbonate (AN-61, 23.6 mg, 0.09 mmol), and DIPEA (24 µL, 0.14 mmol) in tetrahydrofuran (THF, 6 mL) was stirred at room temperature for 48 h. The solvents were removed under vacuum and the residue was diluted with ethyl acetate and washed sequentially with aqueous NaHCO₃, aqueous KHSO₄, brine, dried on Na₂SO₄, and concentrated in vacuo. The residue was purified using preparative TLC (chloroform:methanol, 9:1). Crystallization from ethyl acetate and hexane (1:2) provided 40 mg (78%) of AN-92; mp 204°–205° C.; TLC [R_f=0.47 (chloroform:methanol, 9:1)]; HPLC (rt=10.6 min.); MS m/z 554 (M+H)⁺; ¹H NMR (CD₃OD); d 1.68–1.74 (m, 1H), 1.77–1.82 (m, 1H), 1.92 (s, 3H), 2.67 (dd, J=13.5; 8.7 Hz, 1H), 2.83 (dd, J=13.5; 5.6 Hz, 1H), 2.87 (d, J=7.7 Hz, 2H), 3.78–3.82 (m, 1H), 4.11–4.16 (m, 1H), 4.48–4.52 (m, 1H), 4.99–5.07 (m, 2H), 6.47 (d, J=7.3 Hz, 1H), 6.76 (d, J=7.7 Hz, 1H) 6.94 (t, J=7.8 Hz, 1H), 7.12–7.30 (m, 10H), 7.37–7.40 (m, 1H), 7.69–7.72 (m, 1H), 8.44–8.46 (m, 1H), 8.48–8.49 (m, 1H).

EXAMPLE 5

The compound (2S,3R,4S,5S)-2-[N-(N-benzyloxycarbon-yl)valinyl)amino]-5-[N-[N-((2-pyridinyl methoxy)carbonyl)anthranilyl]amino]-3,4-dihydroxy-1,6-diphenyl hexane (DN-14) was prepared as follows. DIPEA (315 mg, 425 mL, 3.9 mmol) was added to a stirred solution of the trifluoroacetate salt of (2S,3R,4S,5S)-2-amino-5-[N-[N-((2-pyridinylmethoxy)carbonyl)anthranilyl]amino]-3,4-dihydroxy-1,6-diphenyl hexane (LL-113, 0.76 mmol), TBTU (245 mg, 0.76 mmol), HOBT (117 mg, 0.76 mmol) and N-benzyloxycarbonyl valine (212 mg, 0.85 mmol), in 50 mL of DMF. The reaction mixture was stirred at room temperature for 2 h. The solvents and volatiles were removed under reduced pressure. Addition of ethyl acetate (200 mL) to the residue provided LL-75 as a white solid, which was collected by filtration and washed with mixture methanol/ethyl acetate (1:1, 300 mL). Yield 220 mg. The filtrate was evaporated under reduced pressure, residue was taken up in ethyl acetate and washed sequentially with aqueous KHSO₄ (pH=5), brine, aqueous NaHCO₃, and brine. The organic layer was dried over Na₂SO₄ and concentrated under reduced pressure to provide crude DN-14. Combined yield; 540 mg (86%); mp 187° C. (decompose); TLC [Rf=0.45 (chloroform:methanol, 95:5)]; HPLC (rt= 22.0 min.), MS m/z 810(M+Na)⁺; ¹H NMR (CD₃OD/DMSO-d₆) d 0.76–0.78 (m, 6H), 1.89–1.93 (m, 1H), 2.79–2.84 (m, 1H), 2.91–2.92 (m, 2H), 2.95–2.99 (m, 1H), 3.61 (m, 2H), 4.42–4.52 (m, 2H), 4.70–4.73 (m, 1H), 5.03–5.04 (m, 2H), 5.15–5.24 (m, 2H), 7.00–7.03 (m, 1H), 7.07–7.46 (m, 23H), 7.82–7.85 (m, 1H), 7.14–7.15 (m, 1H), 8.52 (m, 1H).

EXAMPLE 6

The compound (2S,3R,4S,5S)-2-[N-(N-(2-pyridinylmethoxy)valinyl)amino]-5-[N-[N-((2-pyridinyl methoxy)carbonyl)anthranilyl]amino]-3,4-dihydroxy-1,6-diphenyl hexane (LL-73) was prepared as follows. DIPEA (39 mg, 52 mL, 0.3 mmol) was added to a stirred solution of the trifluoroacetate salt of (2S,3R,4S,5S)-2-amino-5-[N-[N-((2-pyridinylmethoxy)carbonyl)anthranilyl]amino]-3,4-dihydroxy-1,6-diphenyl hexane (LL-113, 0.075 mmol), TBTU (25 mg, 0.076 mmol), HOBT (12 mg, 0.076 mmol) and [N-(2-pyridinylmethoxy)carbonyl] valine (22 mg, 0.085 mmol) in DMF (10 mL). The reaction mixture was stirred at room temperature for 2 h. The solvents and volatiles were removed under reduced pressure, residue was taken up in ethyl acetate, washed sequentially with aqueous KHSO₄ (pH=5), brine, aqueous NaHCO₃, and brine. The organic layer was dried over Na₂SO₄ and concentrated under reduced pressure to provide crude LL-73. Yield 45 mg (81%); mp 198°–199° C.; TLC [Rf=0.29 (chloroform:methanol, 95:5)]; HPLC (rt=18.3 min.); MS m/z 811(M+Na)⁺; ¹H NMR (DMSO-d₆) d 0.70 (s, 3H), 0.72 (s, 3H), 1.9 (m, 1H), 2.76–2.88 (m, 4H), 3.45–3.54 (m, 2H), 3.86–3.89 (m, 1H), 4.26–4.31 (m, 1H), 4.60–4.63 (m, 1H), 4.88 (d, J=4.4 Hz, 1H), 5.02–5.21 (m, 4H), 5.41 (d, J=6.6 Hz, 1H), 7.03–7.09 (m, 2H), 7.12–7.38 (m, 15H), 7.42–7.45 (m, 1H), 7.64 (d, J=7.6 Hz, 1H), 7.74–7.83 (m, 3H), 8.13 (d, J=8.5 Hz, 1H), 8.29 (d, J=9.2 Hz, 1H), 8.50 (d, J=4.3 Hz, 1H), 8.55 (d, J=4.7 Hz, 1H), 10.72 (s, 1H).

EXAMPLE 7

The compound (2S,3S,5S)-2-[N-(N-(2-pyridinylmethoxy)valinyl)amino]-5-[N-[N-((2-pyridinyl methoxy)carbonyl)anthranilyl]amino]-1,6-diphenyl-3-hydroxy hexane (LL-75) was prepared as follows. The synthesis began with the preparation of (2S,3S,5S)-5-[N-(tert-butyloxycarbonyl)amino]-2-[N-(N-(2-pyridinylmethoxy)valinyl) amino]-1,6-diphenyl-3-hydroxy hexane (LL,-74). DIPEA (48 mg, 64 mL, 0.37 mmol) was added to a stirred solution of (2S,3S,5S)-2-amino-5-[N-(tert-butyloxycarbonyl)amino]-1,6-diphenyl-3-hydroxy hexane (RS-216, 70 mg, 0.18 mmol), TBTU (59 mg, 0.18 mmol), HOBT (28 mg, 0.18 mmol) and N-[(2-pyridinylmethoxy) carbonyl] valine (47 mg, 0.2 mmol), in DMF (20 mL). The reaction mixture was stirred at room temperature for 2 h. The solvent and volatiles were removed under reduced pressures residue taken up in ethyl acetate and washed sequentially with aqueous KHSO₄ (pH=5), brine, aqueous NaHCO₃ and brine. The organic layer was dried over Na₂SO₄ and concentrated under reduced pressure to provide crude LL-74 which was used in next step with out further purification. Yield 108 mg (99%); TLC [Rf=0.62 (chloroform:methanol, 9:1)]; HPLC (rt=20.37 min.); MS m/z 627 (M+Na)⁺;

The compound (2S,3S,5S)-5-amino-2-[N-(N-(2-pyridinyl-methoxy)valinyl)amino]-1,6-diphenyl-3-hydroxy hexane hydrochloride salt (LL-74A) was prepared from LL-74. The compound (2S,3S,5S)-5-[N-(tert-butyloxycarbonyl)amino]-2-[N-(N-(2-pyridinylmethoxy)valinyl)amino]-1,6-diphenyl-3-hydroxy hexane (LL-74, 108 mg, 0.183 mmol) was dissolved in 4.0M solution of HCl in dioxane (20 ml), and stirred at room temperature for 30 min. after which solvents were evaporated. The evaporation was repeated 3 times with ethyl ether (10 ml) and finally dried under vacuum. This compound (LL-74A) was used in next step without further purification. TLC [R$_f$=0.35 (chloroform:methanol, 8:2)]; HPLC (rt=12.6 min.); MS m/z 505 (M+H)⁺.

The compound (2S,3S,5S)-2-[N-(N-(2-pyridinylmethoxy)valinyl)amino]-5-[N-[N-((2-pyridinylmethoxy) carbonyl)anthranilyl] amino]-1,6-diphenyl-3-hydroxy hexane (LL-75) was prepared from LL-74A. DIPEA (94 mg, 127 mL, 0.7 mmol) was added to a stirred solution of hydrochloride salt of (2S,3S,5S)-5-amino-2-[N-(N-(2-pyridinyl-methoxy)valinyl)amino]-1,6-diphenyl-3-hydroxy hexane (LL-74A, 0.18 mmol), TBTU (59 mg, 0.18 mmol), HOBT (28 mg, 0.18 mmol) and N-[(2-pyridinylmethoxy)-carbonyl]anthranilic acid (55 mg, 0.2 mmol), DMF (20 mL). The reaction mixture was stirred at room temperature for 4 h. The solvent and volatiles were removed under reduced pressure, residue taken up in ethyl acetate and washed sequentially with aqueous KHSO₄ (pH= 5), brine, aqueous NaHCO₃ and brine. The organic layer was dried over Na₂SO₄ and concentrated under reduced pressure to provide crude LL-75. Purified by preparative TLC (chloroform:methanol, 10:1); Yield 73 mg (53%); mp 198°–199° C.; TLC [R$_f$=0.31 (chloroform:methanol, 95:5)]; HPLC (rt=18.5 min.); MS m/z 773(M+H)⁺; ¹H NMR (CD₃OD) d 0.83 (d, J=3.9 Hz, 3H), 0.82 (d, J=3.7 Hz, 3H), 1.71–1.74 (m, 2H), 1.92–1.99 (m, 1H), 2.58–2.89 (m, 4H), 3.72–3.75 (m, 1H), 3.81–3.86 (m, 1H), 4.38–4.41 (m, 1H), 4.45–4.51 (m, 1H), 5.08–5.25 (m, 4H), 6.98–7.02 (m, 2H), 7.07–7.11 (m, 3H), 7.17–7.21 (m, 6H), 7.28–7.33 (m, 3H), 7.38–7.47 (m, 3H), 7.75 (dt, J=7.8; 1.7 Hz, 1H), 7.82 (dt, J=7.8; 1.4 Hz, 1H), 8.14 (d, J=8.3 Hz, 1H), 8.45–8.48 (m, 2H).

EXAMPLE 8

The compound (2S,3S,5S)-2-[N-[(3-hydroxy-2-methylphenyl)carbonyl]amino]-5-[N-[N-[(2-pyridinylmethoxy)carbonyl]anthranilyl]amino]-1,6-diphenyl-3-hydroxy hexane (LL-82) was prepared as follows. Compound (2S,3S,5S)-5-[N-[(tertbutyloxy)carbonyl]amino]-2-[N-[(3-hydroxy-2-methylphenyl)carbonyl]amino]-1,6-diphenyl-3-hydroxy hexane (RS-208, 52 mg, 0.1 mmol) was dissolved in 4.0M HCl in dioxane (15 mL) and stirred at room temperature for 30 min. after which solvents were evaporated. The evaporation was repeated 3 times with ethyl ether (10 mL) and finally dried under vacuum. This compound, (2S,3S,5S)-5-amino-2-[N-[(3-hydroxy-2-methylphenyl)carbonyl]amino]-1,6-diphenyl-3-hydroxy hexane hydrochloride salt (LL-81) was used in next step with out further purification. TLC [R$_f$=0.22 chloroform:methanol, 1:1)]; HPLC (rt=9.6 min.); MS m/z 519 (M+H)⁺.

DIPEA (43 mg, 56 mL, 0.31 mmol) was added to a stirred solution of hydrochloride salt of (2S,3S,5S)-5-amino-2-[N-[(3-hydroxy-2-methylphenyl)carbonyl]amino]-1,6-diphenyl-3-hydroxy hexane (LL-81, 0.1 mmol), TBTU (32.1 mg, 0.1 mmol), HOBT (15.3 mg, 0.1 mmol) and N-[(2-pyridinyl methoxy)carbonyl]anthranilic acid (32 mg, 0.11 mmol), in DMF (20 mL). The reaction mixture was stirred at room temperature for 4 h. After that, the reaction was quenched with a drop of 4-(2-aminoethyl)morpholine and the stirring continued for addition 15 min. The solvent and volatiles were removed under reduced pressure, residue was taken up in ethyl acetate and washed sequentially with aqueous KHSO₄ (pH=5), brine, aqueous NaHCO₃ and brine. The organic layer was dried over Na₂SO₄ and concentrated under reduced pressure to provide crude LL-82. The crude LL-82 was purified by preparative TLC (chloroform:methanol, 95:5); Yield 53 mg (80%); mp 161°–162° C.; TLC [R$_f$=0.28 (ethyl acetate:hexane, 2:1)]; HPLC (rt=17.5 min.); MS m/z 673 (M+H)⁺; ¹H NMR (DMSO-d₆) d 1.83–1.87 (m, 2H), 1.94 (s, 3H), 2.78–2.95 (m, 4H), 3.78–3.82 (m, 1H), 4.22 (s, 1H), 4.58–5.05 (m, 2H), 5.17–5.27 (m, 2H), 6.51–6.53 (m, 1H), 6.77–6.79 (m, 1H), 6.93–6.98 (m, 1H), 7.03–7.32 (m, 13H), 7.41–7.48 (m, 3H), 7.74 (dt, J=7.6; 1.8 Hz, 1H), 8.18–8.21 (m, 1H), 8.49–8.51 (m, 1H).

EXAMPLE 9

The compound (2S,3S,5S)-5-[N-[N-((2-pyridinylmethoxy)carbonyl)anthranilyl]amino]2-[N-((3-S-(tetrahydrofuranyl)oxy)carbonyl)amino]-1,6-diphenyl-3-hydroxy hexane LL-101 was prepared as follows. Compound (2S,3S,5S)-5-[N-(tert-butyloxycarbonyl)amino]-2-[N-((9-fluorenylmethoxy)carbonyl)amino]-1,6-diphenyl-3-hydroxy hexane (LL-87) was first prepared. 9-fluorenylmethyl-N-succinimidyl carbonate (Fmoc-OSu, 1.85 g, 5.5 mmol) was added to a stirred solution of (2S,3S,5S)-2-amino-5-[N-(tert-butyloxycarbonyl)amino]-1,6-diphenyl-3-hydroxy hexane (RS-216, 2 g, 5.2 mmol) in of methylene chloride (120 mL). The reaction mixture was stirred at room temperature for 3 h. The solvent was removed under reduced pressure, residue was taken up in methylene chloride and washed sequentially with aqueous KHSO₄, brine, aqueous NaHCO₃, and brine. The organic layer was dried over MgSO₄ and concentrated under reduced pressure to provide crude LL-87. The crude product was crystallized from chloroform:methanol:hexane (1:1:4); Yield 3.0 g (95%); mp 140°–141° C.; TLC [R$_f$=0.35 (ethyl acetate:hexane, 2:1)]; HPLC (rt=26.7 min.); MS m/z 629 (M+Na)⁺; ¹H NMR (CDCl₃) d 1.39 (s, 9H), 1.62 (m, 2H), 2.72–2.74 (m, 2H), 2.82–2.86 (m, 2H), 3.66–3.85 (m, 3H), 4.12–4.29 (m, 1H), 4.31–4.52 (m, 2H), 5.08 (d, J=3.2 Hz, 1H), 7.07–7.32 (m, 14H), 7.37–7.42 (m, 2H),7.51–7.56 (m, 2H), 7.75–7.77 (m, 2H).

Compound (2S,3S,5S)-5-amino-2-[N-((9-fluorenylmethoxy)carbonyl)amino]-1,6-diphenyl-3-hydroxy hexane TFA salt (LL-96) was prepared. Compound (2S,3S,5S)-5-[N-(tert-butyloxy carbonyl)amino]-2-[N-((9-fluorenylmethoxy)carbonyl)amino]-1,6-diphenyl-3-hydroxy hexane (LL-87, 787 mg, 1.3 mmol) was dissolved in trifluoroacetic acid (10 mL), and stirred at room temperature for 10 min. after which solvents were evaporated. The evaporation was repeated 3 times with ethyl ether (10 mL) and finally dried under vacuum. This compound (LL-96) was used in next step with out further purification.

Compound (2S,3S,5S)-2-[N-((9-fluorenylmethoxy) carbonyl)amino]-5-[N-[N-((2-pyridinylmethoxy) carbonyl) anthranilyl]amino]-1,6-diphenyl-3-hydroxy hexane (LL-89) was then prepared as follows. DIPEA (387 mg, 521 mL, 3.9 mmol) was added to a stirred solution of the (2S,3S,5S)-5-amino-2-[N-((9-fluorenylmethoxy)carbonyl)amino]-1,6-diphenyl-3-hydroxy hexane TFA salt (LL-96, 1.3 mmol), TBTU (417 mg, 1.3 mmol), HOBT (198 mg, 1.3 mmol) and N-[(2-pyridinylmethoxy)carbonyl]anthranilic acid (389 mg, 1.4 mmol) in DMF (50 mL). The reaction mixture was stirred at room temperature for 2 h. The solvents and volatiles were removed under reduced pressure, residue was taken up in ethyl acetate and concentrated under reduced pressure and washed sequentially with aqueous $KHSO_4$ (pH=5) brine, aqueous $NaHCO_3$, and brine. The organic layer was dried over $Na_2SO_4$ and concentrated under reduced pressure to provide crude LL-89. Yield 900 mg (90%); mp 149°–150° C.; TLC [$R_f$=0.39 (ethyl acetate:hexane, 2:1)]; HPLC (rt=25.8 min.); MS m/z 783 (M+Na)$^+$; $^1$H NMR (CDCl$_3$) d 1.73 (m, 2H), 2.85–2.89 (m, 4H), 3.5–3.8 (m, 2H), 4.11 (m, 1H), 4.29–4.37 (m, 3H), 5.11 (m, 1H), 5.21–5.26 (m, 2H), 6.53 (d, J=7.2 Hz, 1H), 6.93–6.98 (m, 1H), 7.15–7.51 (m, 22H), 7.63–7.75 (m, 4H), 8.33 (d, J=8.2 Hz, 1H), 8.52 (d, J=4.2 Hz, 1H).

Compound (2S,3S,5S)-2-amino-5-[N-[N-((2-pyridinylmethoxy)carbonyl)anthranilyl]amino]-1,6-diphenyl-3-hydroxy hexane (LL-100) was prepared as follows. (2S,3S,5S)-2-[N-((9-fluorenylmethoxy) carbonyl) amino]-5-[N-[N-((2-pyridinylmethoxy)carbonyl) anthranilyl]amino]-1,6-diphenyl-3-hydroxy hexane (LL-89, 107 mg, 0.14 mmol) was dissolved in methylene chloride (20 mL) containing 20% of piperidine and stirred at room temperature for 20 min., after which solvents were evaporated residue was suspended in hexane (60 mL) and filtered. The resulting solid was dissolved in chloroform (30 mL) and washed with water. The organic layer was dried over $Na_2SO_4$ and concentrated under reduced pressure to provide crude LL-100. This compound was used in next step without further purification. TLC [$R_f$=0.22 (chloroform:methanol, 9:2)]; HPLC (rt=13.5 min.); MS m/z 559 (M+Na)$^+$; $^1$H NMR (CD$_3$OD) d 1.73–1.93 (m, 2H), 2.67–3.02 (m, 4H), 3.65–3.73 (m, 1H), 4.3–4.5 (m, 1H), 5.23 (s, 1H), 6.96–7.49 (m, 16H), 7.82 (dt, J=6.6; 1.7 Hz, 1H), 8.14 (dd, J=8.4; 0.7 Hz, 1H), 8.48–8.52 (m, 1H).

(3-S-tetrahydrofuranyl)-N-succiimidyl carbonate (AN-65, 42 mg, 0.18 mmol) was added to a stirred solution of (2S,3S,5S)-2-amino-5-[N-[N-((2-pyridinylmethoxy) carbonyl) anthranilyl]amino]-1,6-diphenyl-3-hydroxy hexane (LL-100, 0.14 mmol) in methylene chloride (25 mL). The reaction mixture was stirred at room temperature for 3 h. Solvent was removed under reduced pressure, residue was taken up in methylene chloride and washed sequentially with aqueous $KHSO_4$ (pH=5), brine, aqueous $NaHCO_3$, and brine. The organic layer was dried over $Na_2SO_4$ and concentrated under reduced pressure to provide crude (2S,3S, 5S)-5-[N-[N-((2-pyridinylmethoxy)carbonyl)anthranilyl] amino]2-[N-((3-S-(tetra hydrofuranyl)oxy)carbonyl)amino]-1,6-diphenyl-3-hydroxy hexane (LL-101). Purified by preparation TLC, (chloroform:methanol, 9:1); Yield 60 mg (66%); mp 140°–141° C.; TLC [$R_f$=0.30 (ethyl acetate:hexane, 2:1)]; HPLC (rt=17.7 min.), MS m/z 675 (M+Na)$^+$; $^1$H NMR (CDCl$_3$) d 1.73–1.78 (m, 2H), 1.90–1.95 (m, 1H), 2.08–2.14 (m, 1H), 2.84–2.85 (m, 2H), 2.90–2.91 (m, 2H), 3.66–3.87 (m, 6H), 4.33–4.40 (m, 1H), 5.02–5.04 (d, J=9.1 Hz, 1H), 5.14 (m, 1H), 5.25–5.32 (m, 2H), 6.41–6.46 (m, 1H), 6.95–6.98 (m, 1H), 7.14–7.28 (m, 13H), 7.41–7.44 (m, 2H), 7.67–7.70 (m, 1H), 8.32 (d, J=8.4 Hz, 1H), 8.55–8.56 (m, 1H).

EXAMPLE 10

This Example illustrates the synthesis of (2S,3S,5S)-2-[N-[(3-hydroxy-2-methylphenyl)carbonyl]amino]-5-[N-(3-aminophenyl)carbonyl]amino-1,6-diphenyl-3-hydroxy hexane (AN-96).

Compound (2S,3S,5S)-5-[N-(tert-butyloxycarbonyl) amino]-2-[N-[(3-hydroxy-2-methylphenyl)carbonyl]amino-1,6-diphenyl-3-hydroxy hexane (RS-208, 260 mg, 0.5 mmol) was dissolved in 4.0M solution of HCl in dioxane (50 mL) and stirred at room temperature for 30 min. after which solvents were evaporated. The evaporation was repeated 3 times with ethyl ether (30 mL) and finally dried under vacuum. Yield, 217 mg (96%) of (2S,3S,5S)-5-Amino-2-[N-[(3-hydroxy-2-methylphenyl)carbonyl]amino]-1,6-diphenyl-3-hydroxy hexane hydrochloride salt (AN-87); TLC [Rf=0.22 (chloroform:methanol, 1:1)]; HPLC (rt=9.6 min.); mp 234°–235° C., MS m/z 419 (M+H)$^+$; $^1$H NMR (CDCl$_3$/CD$_3$OD), d 1.75–1.94 (m, 2H), 2.03 (s, 3H), 2.83–3.03 (m, 4H), 3.37–3.40 (m, 1H), 3.84–3.90 (m, 1H), 4.21–4.32 (m, 1H), 6.68 (dd, J=7.7; 0.9 Hz, 1H), 6.81 (dd, J=7.8; 0.9 Hz, 1H), 6.90 (dd, J=7.8; 7.8 Hz, 1H), 7.18–7.38 (m, 10H).

Compound (2S,3S,5S)-2-[N-(3-hydroxy-2-methylphenyl)carbonyl]amino-5-[N-(3-nitrophenyl) carbonyl] amino-3-hydroxy-1,6-diphenyl hexane (AN-95) was prepared from AN-87. A solution of (2S,3S,5S)-2-[N-[(3-hydroxy-2-methylphenyl)carbonyl]amino]-5-amino-1,6-diphenyl-3-hydroxy hexane hydrochloride salt (AN-87, 82 mg, 0.18 mmol) and 3-nitrobenzoic acid (24.3 mg, 0.18 mmol), TBTU(57.8 mg, 0.18 mmol), HOBT (55.1 mg, 0.36 mmol) and DIPEA(94 µL, 0.54 mmol) in DMF (10 mL) was stirred at room temperature for 6 h. The solvents were removed under vacuum and the residue was diluted with ethyl acetate and washed sequentially with aqueous $NaHCO_3$, aqueous $KHSO_4$, brine, dried on $Na_2SO_4$, and concentrated in vacuo. Crystallization from methylene chloride and hexane (1:2) provided 85 mg (83%) of white solid (AN-95); mp 194°–195° C.; TLC [$R_f$=0.56 (chloroform:methanol, 9:1)]; HPLC (rt=17.8 min.); MS m/z 568 (M+H)$^+$; $^1$H NMR (CDCl$_3$/CD$_3$OD); d 1.80–1.93 (m, 2H), 2.06 (s, 3H), 2.91–3.03 (m, 4H), 3.76–3.80 (m, 1H), 4.19–4.23 (m, 1H), 4.31–4.37 (m, 1H), 6.57–6.59 (m, 1H), 6.79–6.81 (m, 10H), 6.97 (dd, J=7.8; 7.8 Hz, 1H), 7.14–7.35 (m, 10H), 7.61 (dd, J=8.0; 8.0 Hz, 1H), 8.02 (ddd, J=8.0;1.5; 1.1 Hz, 1H), 8.33 (ddd, J=8.2; 2.2; 1.0 Hz, 1H), 8.52 (dd, J=1.8; 1.8 Hz, 1H).

Compound (2S,3S,5S)-5-[N-[(3-aminophenyl)carbonyl] amino]2-[N-[(3-hydroxy-2-methylphenyl) carbonyl]amino]-1,6-diphenyl-3-hydroxy hexane (AN-96) was prepared from AN-95. The mixture of (2S,3S,5S)-2-[N-[(3-hydroxy-2-methylphenyl)carbonyl]amino]-5-[N-[(3-nitrophenyl) carbonyl]amino]-1,6-diphenyl-3-hydroxy hexane (AN-95, 65 mg, 0.11 mmol) and 10% palladium on carbon (15 mg in ethanol (20 mL) was stirred under H$_2$ atmosphere for 8 h. The resulting mixture was filtered through the filtering agent Celite 521, washed with ethanol and concentrated in vacuo. Crystallization from ethyl acetate:hexane (1:2) gave 55 mg (93%) of AN-96; mp 201°–201° C.; TLC [$R_f$=0.42 (chloroform:methanol, 9:1)]; HPLC (rt=11.4 min); MS m/z 538 (M+H)$^+$; $^1$H NMR (CDCl$_3$/CD$_3$OD), d: 1.76–1.87 (m, 2H), 2.04 (s, 3H), 2.88–3.01 (m, 4H), 3.77–3.81 (m, 1H), 4.21–4.26 (m, 1H), 4.29–4.35 (m, 1H), 6.55–6.57 (m, 1H), 6.78–6.82 (m, 2H), 6.94–6.98 (m, 3H), 7.14–7.28 (m, 11H).

EXAMPLE 11

This example illustrates the synthesis of (2S,3S,5S)-2-[N-[(3-hydroxy-2-methylphenyl)carbonyl]amino]-5-[N-(3-S-(tetra hydrofuranyl)oxy)carbonyl]amino]-1,6-diphenyl-3-hydroxy hexane (AN-98).

A solution of (2S,3S,5S)-2-[N-[(3-hydroxy-2-methylphenyl)carbonyl]amino]-5-amino-1,6-diphenyl-3-hydroxy hexane hydrochloride salt (AN-87, 70.5 mg, 0.15 mmol) and (3-S-tetrahydrofuranyl)-N-succiimidyl carbonate (AN-65, 38.9 mg, 0.15 mmol), and DIPEA (40 µl, 0.23 mmol) in acetonitrile (CH$_3$CN, 10 ml) was stirred at room temperature for 2 h. The solvents were removed under vacuum and the residue was diluted with ethyl acetate and washed sequentially with aqueous NaHCO$_3$, aqueous KHSO$_4$, brine, dried on Na$_2$SO$_4$, and concentrated in vacuo. Crystallization from ethyl acetate:hexane (1:2) provided 65 mg (80%) of AN-98; mp 224°–225° C.; TLC [R$_f$=0.63 (ethyl acetate:hexane, 2:1)]; HPLC (rt=14.5 min.); MS m/z 533 (M+H)$^+$; $^1$H NMR (CD$_3$OD); d 1.67–1.73 (m, 1H), 1.76–1.81 (m, 1H), 1.88–1.99 (m, 1H), 1.94 (s, 3H), 2.07–2.15 (m, 1H), 2.66 (dd, J=13.5; 8.6 Hz, 1H), 2.82 (dd, J=13.5; 5.3 Hz, 1H), 2.89 (dd, J=13.5; 9.5 Hz, 1H), 2.94 (dd, J=13.6; 5.9 Hz, 1H), 3.55 (d, J=10.2 Hz, 1H), 3.73–3.84 (m, 4H), 4.06–4.11 (m, 1H), 4.47–4.51 (m, 1H), 5.03–5.04 (m, 1H), 6.48 (d, J=7.4 Hz, 1H), 6.76 (d, J=7.9 Hz, 1H), 6.94 (t, J=7.8 Hz, 1H), 7.14–7.32 (m, 10H).

EXAMPLE 12

This example describes the antiretroviral activity of compounds prepared in accordance with the above examples.

The inhibition constants (K$_i$) for the compounds of the above examples were determined using purified HIV-1 protease (wild-type, WT) (Tables I, II and III). K$_i$ is an inhibition constant of a given compound as derived by enzyme kinetics. A low K$_i$ represents a high affinity of the compound for the enzyme, i.e., tight binding or low dissociation. Inhibition of the cleavage was assayed using a fluorogenic substrate available from Molecular Probes, Inc., Eugene, Oreg., and described in Kageyama et al., *Antimicrob. Agents. Chemother.*, 37, 272 (1993), and a fluorogenic substrate available from Bachem California, Torrance, Calif., and described in Kageyama et al. (1993), supra. The inhibitory potencies of these compounds are set forth in Tables I–III. Percent inhibition is the percentage inhibition of an enzyme's activity by a given compound at a given concentration.

TABLE I

Asymmetric HIV Protease inhibitors

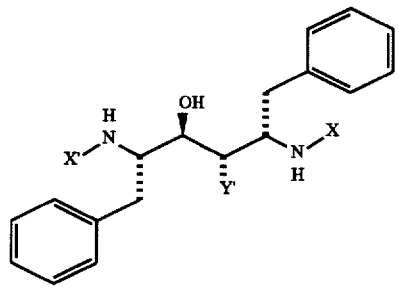

| compound | X' | X | Y' | MWt | logP | K$_i$ (nM) | EC$_{50}$ µM | IC$_{50}$ µM |
|---|---|---|---|---|---|---|---|---|
| RS-205 |  |  | OH | 528 | 3.560 | 4.6 | 16 | >150 |
| AN-89 |  |  | H | 538 |  | 1.88 |  |  |
| AN-88 |  |  | H | 538 |  | 3.65 |  |  |
| RS-208 |  |  | H | 518 |  | 0.213 | 0.47 | 23 |

TABLE I-continued

Asymmetric HIV Protease inhibitors

[Structure: central chain with X'-NH-CH(CH2Ph)-CH(OH)-CH(Y')-CH(CH2Ph)-NH-X, stereochemistry indicated]

| compound | X' | X | Y' | MWt | logP | K$_i$ (nM) | EC$_{50}$ μM | IC$_{50}$ μM |
|---|---|---|---|---|---|---|---|---|
| Diol-51 | 4-HO-C6H4-C(O)- | 4-HO-C6H4-C(O)- | OH | 540 | | 276 | | |
| Diol-58 | 2-HO-C6H4-C(O)- | 2-HO-C6H4-C(O)- | OH | 540 | | 32% 10μ | | |
| AN-72 | 2-NH2-C6H4-C(O)- | 2-NH2-C6H4-C(O)- | H | 522 | | 96 | | |
| AN-92 | 3-HO-2-Me-C6H3-C(O)- | 3-pyridylmethyl-O-C(O)- | H | 553 | | 0.46 | 1.3 | >100 |
| AN-98 | 3-HO-2-Me-C6H3-C(O)- | (tetrahydrofuran-3-yl)-O-C(O)- | H | 532 | | 0.32 | 0.63–1 | >100 |
| AN-106 | 3-HO-2-Me-C6H3-C(O)- | 5-HO-2-Me-C6H3-C(O)- | H | 552 | | | | |
| AN-96 | 3-HO-2-Me-C6H3-C(O)- | 3-H2N-C6H4-C(O)- | H | 537 | 4.213 | 0.75 | 0.63–58 | >100 |
| AN-91 | 3-HO-2-Me-C6H3-C(O)- | 4-MeO-C6H4-SO2- | H | 588 | | 1.5 μM | | |

TABLE I-continued

Asymmetric HIV Protease inhibitors

| compound | X' | X | Y' | MWt | logP | $K_i$ (nM) | $EC_{50}$ μM | $IC_{50}$ μM |
|---|---|---|---|---|---|---|---|---|
| Diol-56 | phenyl ketone | phenyl ketone | OH | 508 | | 40 | | |
| Diol-10 | 3-hydroxyphenyl ketone | 3-hydroxyphenyl ketone | OH | 540 | 3.809 | 22/25 | | |
| Diol-52 | 3-hydroxy-2-methylphenyl ketone | 3-hydroxy-2-methylphenyl ketone | OH | 568 | 4.889 | 1.2 | 0.9 | 25 |
| Diol-57 | 2-methylphenyl ketone | 2-methylphenyl ketone | OH | 536 | | 8 | | |
| RS-194 | (S)-tetrahydrofuranyl carbonate | (S)-tetrahydrofuranyl carbonate | H | 512 | 3.560 | 1.68 | 6.5 | >50 |
| RS-196 | t-butyl carbamate | t-butyl carbamate | OH | 500 | | 8.4 | | |
| RS-199 | 3-hydroxy-2-methylphenyl ketone | t-butyl carbamate | OH | 534 | | 0.66 | 1.3 | >50 |
| RS-198 | t-butyl carbamate | 3-hydroxy-2-methylphenyl ketone | OH | 534 | | 8.3 | | |

TABLE I-continued

Asymmetric HIV Protease inhibitors

| compound | X' | X | Y' | MWt | logP | $K_i$ (nM) | $EC_{50}$ μM | $IC_{50}$ μM |
|---|---|---|---|---|---|---|---|---|
| AN-76 | (S)-tetrahydrofuranyl ester | 3-hydroxy-2-methylbenzoyl | OH | 548 | | 2.0 | 7.5 | >50 |
| AN-78 | 3-hydroxy-2-methylbenzoyl | (S)-tetrahydrofuranyl ester | OH | 548 | 4.225 | 1.43 | 21 | >50 |
| RS-201 | 5-hydroxy-2-methylbenzoyl | 5-hydroxy-2-methylbenzoyl | H | 552 | | 6.6 | | |
| DD-8 | 3-hydroxy-2-methylbenzoyl | 3-hydroxy-2-methylbenzoyl | H | 552 | | 0.8 | 0.4 | 22 |
| AN-105 | 3-hydroxy-2-methylbenzoyl | (2-pyridylmethoxycarbonyl)-valyl | H | 652 | | | | |

TABLE II

Asymmetric anthranilamide containing HIV PR inhibitors

| compound | X | Y' | L | MWt | $K_i$ (nM) | $EC_{50}$ μM | $IC_{50}$ μM |
|---|---|---|---|---|---|---|---|
| DN-3 | 3-hydroxybenzoyl | OH | CH | 673 | 5.9 | — | — |
| DN-4 | 3-hydroxybenzoyl | OH | N | 674 | 1.77 | 0.9 | 9–28 |
| DN-6B | 4-aminobenzoyl | OH | N | 669 + 2HCl | 6.6 | — | — |
| DN-11 | t-butoxycarbonyl | OH | N | 654 | 0.45 | 0.49 | 21 |
| AN-43 | t-butylcarbamoyl | H | N | 637 | 1.05 | 1.6 | 33 |
| LL-69 | 3-hydroxy-2-methylbenzoyl | H | N | 672 | 0.68 | | |
| LL-68 | (pyridylmethoxycarbonyl)valyl | H | N | 772 | 0.034 | 0.49 | 22 |
| AN-42 | t-butoxycarbonyl | H | N | 638 | 0.85 | <1 | 23 |

TABLE III

Asymmetric anthranilamide containing HIV PR inhibitors.

| compound | X' | Y | L | MWt | LogP | $K_i$ (pM) | $EC_{50}$ μM | $IC_{50}$ μM |
|---|---|---|---|---|---|---|---|---|
| ND-4 | 3-hydroxybenzoyl | OH | N | 673 | | 760 | — | — |
| LL-70 | tert-butoxycarbonyl-CH₂- | OH | N | 654 | | 140 | — | — |
| DN-14 | (2-pyridylmethoxycarbonyl)-Val- | OH | N | 787 | 6.900 | 4 | .005–.0001 | >100 |
| LL-73 | (2-pyridylmethoxycarbonyl)-Val- | OH | N | 788 | 6.383 | 7 | 0.004 | 47 |
| LL-75 | (2-pyridylmethoxycarbonyl)-Val- | H | N | 772 | 6.466 | 6 | | |
| LL-82 | 3-hydroxy-2-methylbenzoyl | H | N | 672 | 5.813 | 60 ± 18 | 0.033 | 40 |
| LL-101 | (3S)-tetrahydrofuranyloxycarbonyl | H | N | 652 | 5.146 | 42 ± 7 | | |

EXAMPLE 12

This example compares DN-14 with other inhibitors known in the prior art.

| Inhibitors | $K_i$ (pM) | MWt | logP[a] (cal) | $EC_{50}$ (nM) | $IC_{50}$ (µM) | $IC_{50}/EC_{50}$ |
|---|---|---|---|---|---|---|
| DN-14 | 3 | 787 | 6.900 | 6 | >100 | >16,666 |
| KNI-272 | 9.8 | 667 | 6.204 | 28 | >100 | >3,571 |
| Sequinavir | 7 | 670 | 6.195 | 10* | — | — |
| Ritonavir | 9.3 | 717 | 5.622 | 36** | — | — |
| A-77003 | 8.1 | 794 | 5.305 | 140 | >10 | >71 |
| VX-478[b] | 190 | 506 | 3.118 | 40*** | — | — |
| Indinavir | 4 | 613 | 4.476 | 50**** | — | — |

[a]logP values were calculated using HINT.
[b]$EC_{90}$ (M).
*Ho et. al., J. Virol., 68, 2016 (1994).
**Flentge et. al., 207th ACS meeting, Medi., San Deigo (1994).
***Kim et al., J. Am. Chem. Soc., 117, 1181 (1995).
****Dorsey et al., Bioorg. Med. Chem. Lett., 4, 2769 (1994).

EXAMPLE 13

This example demonstrates the anti-retroviral activity of the present inventive compounds in CEM cells.

Using the soluble formazan assay described by Weislow et al. (J. Nat'l. Cancer Inst., 81, 577–586 (1989)), CEM cells chronically infected with HIV-1 were used to assay the anti-retroviral activity of test compounds described herein. The concentration of compound that inhibits 50% of viral activity ($EC_{50}$; determined as described in Weislow et al. (1989), supra) and the inhibition constant ($K_i$, as defined in Example 7) for the compound were determined. DN-14 had a $K_i$ of 4 pM, an $EC_{50}$ of $6.5 \times 10^{-9}$M and, importantly, an $IC_{50} > 100$. These results compared favorably with anti-retroviral compounds currently undergoing clinical trials. For example, KNI272, ABT538, Ro31-8959, and A77003 have $EC_{50}$ values of $4.2 \times 10^{-9}$M, $3.6 \times 10^{-8}$M (Flentge et al., 207th ACS Meeting, San Diego, Calif. (1994)), $1 \times 10^{-8}$M (Ho et al., J. Virol., 68, 2016 (1994) and $2 \times 10^{-7}$ (Ho et al., supra), respectively. These results show that the compounds of the present invention inhibit retroviral activity and have potential utility as retroviral inhibitors. The $IC_{50}/EC_{50}$ shows that the compound DN-14 is not toxic. In addition, the in vitro activity of DN-14 is unaffected in the presence of α-1 acid glycoprotein.

All publications cited herein are hereby incorporated by reference to the same extent as if each publication were individually and specifically indicated to be incorporated by reference and were set forth in its entirety herein.

While this invention has been described with emphasis upon preferred embodiments, it will be obvious to those of ordinary skill in the art that the preferred embodiments may be varied. It is intended that the invention may be practiced otherwise than as specifically described herein. Accordingly, this invention includes all modifications encompassed within the spirit and scope of the appended claims.

What is claimed is:

1. A symmetric or asymmetric antiretroviral compound of the formula:

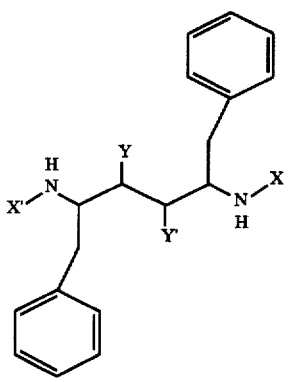

wherein the stereochemistry of each of the benzyl groups on the carbon atoms adjacent to the carbon atoms with the Y and Y' substituents is R or S, Y and Y' are the same or different and are R-hydroxyl, S-hydroxyl or hydrogen; and X and X' are the same or different and are selected from the group consisting of:

(a)

wherein R' is furanyl, tert-butyl or $(CH_2)R''$, wherein R'' is pyridinyl, thiazolyl, morpholinyl, phenyl or phenyl substituted with one or more of a halogen, a hydroxyl, an amino or a $C_1$-$C_4$ alkyl; or (b) a moiety of the formula:

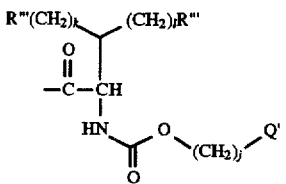

wherein j is 0 to 2, k is 1 to 4, and l is 0 to 4, Q' is phenyl, pyridinyl, thiazolyl, morpholinyl or substituted phenyl; R''' are different and each is hydrogen, a hydroxyl, a halogen, —COOH, —CONH$_2$, an O—$C_{1-4}$ alkyl, SH, a S—$C_{1-4}$ alkyl or a S-aryl; or (c) an N-protected amino acid residue selected from the group consisting of asparagine, histidine, methionine, phenylalanine, threonine, and O-methyl threonine, wherein the N-protecting group is

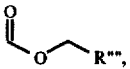

and R'''' is phenyl, pyridinyl, thiazolyl or morpholinyl.

2. The compound of claim 1, wherein said compound is (2S,3R,4S,5S)-2-[N-(N-benzyloxycarbonyl)valinyl)amino]-5-[N-[N-((2-pyridinyl methoxy)carbonyl)anthranilyl] amino]-3,4-dihydroxy-1,6-diphenyl hexane.

3. The compound of claim 1, wherein said compound is (2S,3S,5S)-2-[N-[(3-hydroxy-2-methylphenyl)carbonyl] amino]-5-[N-[N-[(2-pyridinylmethoxy)carbonyl] anthranilyl]amino]-1,6-diphenyl-3-hydroxy hexane.

4. A pharmaceutical composition comprising a retroviral proliferation-inhibiting amount of a compound of claim 1 in a pharmaceutically acceptable carrier.

5. A pharmaceutical composition comprising a retroviral proliferation-inhibiting effective amount of a compound of claim 2 in a pharmaceutically acceptable carrier.

6. A pharmaceutical composition comprising a retroviral proliferation-inhibiting effective amount of a compound of claim 3 in a pharmaceutically acceptable carrier.

7. A method of treating a retroviral infection in a mammal, which method comprises administering to a mammal infected with a retrovirus, the proliferation of which is inhibited by a retroviral proliferation-inhibiting amount of a compound of claim 1, a retroviral proliferation-inhibiting amount of a compound of claim 1 to effect the inhibition of the proliferation of said retrovirus contacted with said retroviral proliferation-inhibiting amount of said compound in said mammal.

8. A method of treating a retroviral infection in a mammal, which method comprises administering to a mammal infected with a retrovirus, the proliferation of which is inhibited by a retroviral proliferation-inhibiting amount of a compound of claim 2, a retroviral proliferation-inhibiting amount of a compound of claim 2 to effect the inhibition of the proliferation of said retrovirus contacted with said retroviral proliferation-inhibiting amount of said compound in said mammal.

9. A method of treating a retroviral infection in a mammal, which method comprises administering to a mammal infected with a retrovirus, the proliferation of which is inhibited by a retroviral proliferation-inhibiting amount of a compound of claim 3, a retroviral proliferation-inhibiting amount of a compound of claim 3 to effect the inhibition of the proliferation of said retrovirus contacted with said retroviral proliferation-inhibiting amount of said compound in said mammal.

* * * * *